(12) United States Patent
Beaton

(10) Patent No.: US 7,077,017 B2
(45) Date of Patent: Jul. 18, 2006

(54) CONTAINER WITH A FRANGIBLE SEAL

(75) Inventor: William F. Beaton, Julian, PA (US)

(73) Assignee: Sigma-Aldrich Co., St. Louis, MO (US)

( * ) Notice: Subject to any disclaimer, the term of this patent is extended or adjusted under 35 U.S.C. 154(b) by 0 days.

(21) Appl. No.: 11/102,114

(22) Filed: Apr. 7, 2005

(65) Prior Publication Data

US 2005/0223823 A1    Oct. 13, 2005

Related U.S. Application Data

(60) Provisional application No. 60/561,747, filed on Apr. 13, 2004.

(51) Int. Cl.
*G01N 1/00* (2006.01)
(52) U.S. Cl. .................... 73/863.23; 220/276
(58) Field of Classification Search ............ 73/864.91, 73/864.34, 863.21, 863.23, 863.25; 220/265–267, 220/270, 274, 275, 276; 215/47, 48, 250, 215/253, 257
See application file for complete search history.

(56) References Cited

U.S. PATENT DOCUMENTS

| | | | | |
|---|---|---|---|---|
| 1,932,291 A | * | 10/1933 | Prefontaine | 169/36 |
| 2,030,617 A | * | 2/1936 | Whitney | 215/250 |
| 3,353,739 A | * | 11/1967 | Schay | 229/123.2 |
| 3,542,240 A | * | 11/1970 | Solowey | 222/83 |
| 3,802,056 A | * | 4/1974 | Jaeger | 29/422 |
| 4,481,297 A | * | 11/1984 | Zucal et al. | 436/181 |
| 5,482,677 A | * | 1/1996 | Yao et al. | 422/88 |
| 6,244,117 B1 | * | 6/2001 | Mengel et al. | 73/863.21 |
| 6,588,619 B1 | * | 7/2003 | Cardarelli | 220/270 |

FOREIGN PATENT DOCUMENTS

WO    WO 80/01558    *    7/1979

OTHER PUBLICATIONS

Vogt, "Application of the Split-Splitless injector to Environmental Analysis", *Journal of Chromatography*, 217 (1981) 91-98.
SUPELCO Bulletin 899A, 1997, cover page and p. 11.
SIGMA-ALDRICH, "ORBO Solvent Desorption Tubes", www.sigmaaldrich.com, 2 pages, admitted prior art.
MPLUS-GmbH, CERTAN®bottles, Updated Aug. 5, 2002, 3 pages.
AMERSHAM Biosciences, Safe and Secure, 2002, cover page and pp. 40-41.
Drawing 1, Splitter (Cup Design) Insert Sleeve, admitted prior art.

* cited by examiner

*Primary Examiner*—Robert Raevis
(74) *Attorney, Agent, or Firm*—Senniger Powers

(57) ABSTRACT

A container for receiving fluids comprises a body having opposite ends and at least one wall defining an interior space. At least one seal defines a sealed chamber within the interior space of the body. Each seal is recessed from one of the ends of the body and has a sealing connection with the wall of the body. A cap sealingly closes each end of the body having a seal recessed therefrom.

18 Claims, 5 Drawing Sheets

CONTAINER WITH A FRANGIBLE SEAL

CROSS-REFERENCE TO RELATED APPLICATIONS

This application claims priority from U.S. Provisional Application Ser. No. 60/561,747 filed Apr. 13, 2004, which is hereby incorporated by reference in its entirety.

BACKGROUND OF THE INVENTION

The present invention relates generally to containers, and more particularly to glass containers having one or more frangible seals.

Sealed glass containers are used in a wide variety of applications. One such application involves the collection of discrete air samples. One common type of air sampling container is formed as a tube having sealed tapered ends. The tube is commonly packed with a sampling media to adsorb or react with one or more target airborne compounds. In practice, the tube remains sealed until just before use thereby ensuring the integrity of the sampling media and the interior space of the tube.

In operation, an air sampling technician, at the desired air sampling location, scores the tapered ends of the air sampling tube with a file and breaks off both of the tapered ends along the score thereby creating an open passage through the interior space of the tube. Next, a free end of polymeric tubing, which is attached to a pump at the other end, is slid over one end of the sampling tube thereby fluidly connecting the sampling tube with the pump. The pump is used to draw a predetermined volume of air to be sampled through the sampling tube. Once the desired volume of air is drawn, the sampling tube is removed from the polymeric tubing and both of its ends are sealed using plastic slide-on caps. The sampling tube is then transported to a laboratory for analysis.

Frequently, breaking off the ends of the sampling tube as described above results in the tube having jagged or uneven edges. These jagged edges pose a risk of injury to the sampling technician. Further, the polymeric tubing may not seal properly with the jagged edges, resulting in leakage between the pump and the tube and potentially compromising the integrity of the air sample. Moreover, the plastic caps used to seal the sampling tube after the air sample has been collected may be cut by the jagged edges thereby potentially resulting in the loss of collected sample or exposing the interior space of the tube to contamination. Accordingly, there is a need for an improved air sampling tube.

Another application for sealed glass containers is the preservation of fluids susceptible to volatilization or evaporation. The shelf-life of many of these fluids can be greatly increased by maintaining the compound in a sealed environment. One know approach is to package the fluid in a sealed glass vial or ampule. When the fluid is needed for use, a glass seal is broken and the fluid is poured from the ampule. Any unused fluid is either transferred to a sealable container for storage or discarded resulting in waste. Accordingly, there is a need for a sealed glass ampule having a cap.

SUMMARY OF THE INVENTION

In general, a container of the present invention comprises a body having opposite ends and at least one wall defining an interior space. At least one seal defines a sealed chamber within the interior space of the body for receiving fluids. Each of the seals has a sealing connection with the wall of the body and is recessed from one of the ends of the body. A cap is used to sealingly close each end of the body having a seal recessed from it.

Another aspect of this invention is a fluid sampling device comprising a tube having a tubular wall defining an interior of the tube, and opposite ends. Seals define a sealed chamber within the tube. The device also has fluid sampling media within the sealed chamber. At least one of the seals comprises a frangible seal. The frangible seal comprises a partition extending across the interior of the tube and having a sealing connection to the tubular wall around a periphery of the partition, a fluid flow opening in the partition, and a frangible sealing element connected to the partition and sealing the opening. The frangible element projects from the partition in a direction away from the sealed chamber. The frangible element is adapted to be selectively broken to open the fluid flow opening for use of the fluid sampling device to sample fluid.

In yet another aspect, this invention is directed to a vial for holding fluids comprising a cylindrical body having a first closed end, a second end opposite the first end, and a wall defining an interior of the body. A seal defines a sealed chamber within the body. A fluid is sealed within the sealed chamber. The seal, which is a frangible seal, comprises a partition extending across the interior of the body and having a sealing connection to the wall around a periphery of the partition, a fluid flow opening in the partition, and a frangible sealing element connected to the partition and sealing the opening. The frangible element projects from the partition in a direction away from the sealed chamber. The frangible element is adapted to be selectively broken to open the fluid flow opening for dispensing the fluid from the vial.

Other objects and features will be in part apparent and in part pointed out hereinafter.

BRIEF DESCRIPTION OF THE DRAWINGS

Corresponding parts are designated by corresponding reference numbers throughout the drawings.

DETAILED DESCRIPTION OF PREFERRED EMBODIMENTS

Figure 1:
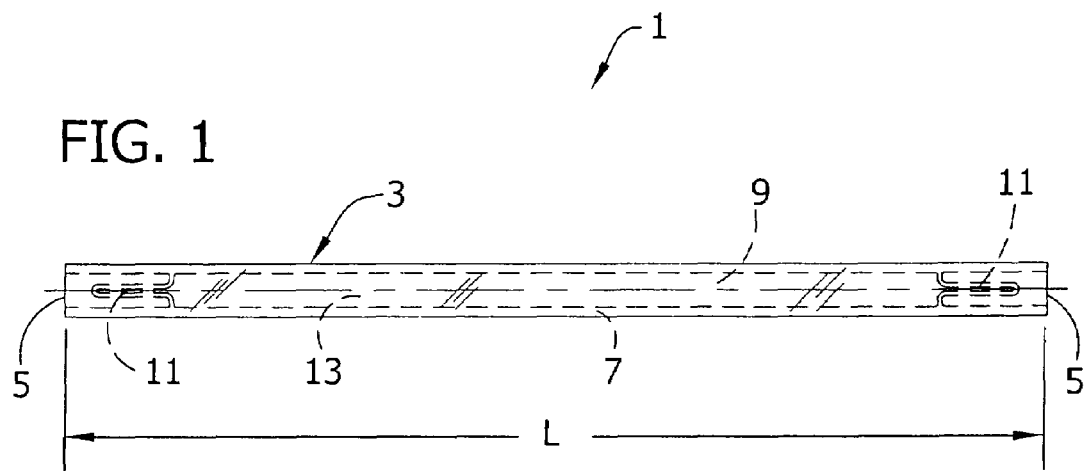
FIG. 1 is a view of one embodiment of an air sampling device of the present invention having two recessed frangible seals.

Referring now to the drawings, FIG. 1 illustrates one embodiment of a container of the present invention, i.e., a fluid sampling device generally designated 1 for sampling fluids including gases (e.g. air) and liquids. The sampling device comprises a tube, indicated generally at 3, having opposite open ends 5 and a tubular wall 7 defining an interior 9 of the tube 3 extending between the opposite ends. Two frangible seals 11 are shown positioned in the interior 9 of the tube 3. The seals 11 are recessed from respective ends 5 of the tube 9 and collectively form a sealed chamber 13 within the interior 9 of the tube 3. The tubular wall 7 of the device may be cylindric or have other non-circular shapes. The illustrated sampling device is made of glass, however it is understood that the device may be made from other suitable frangible materials.

Figure 2:
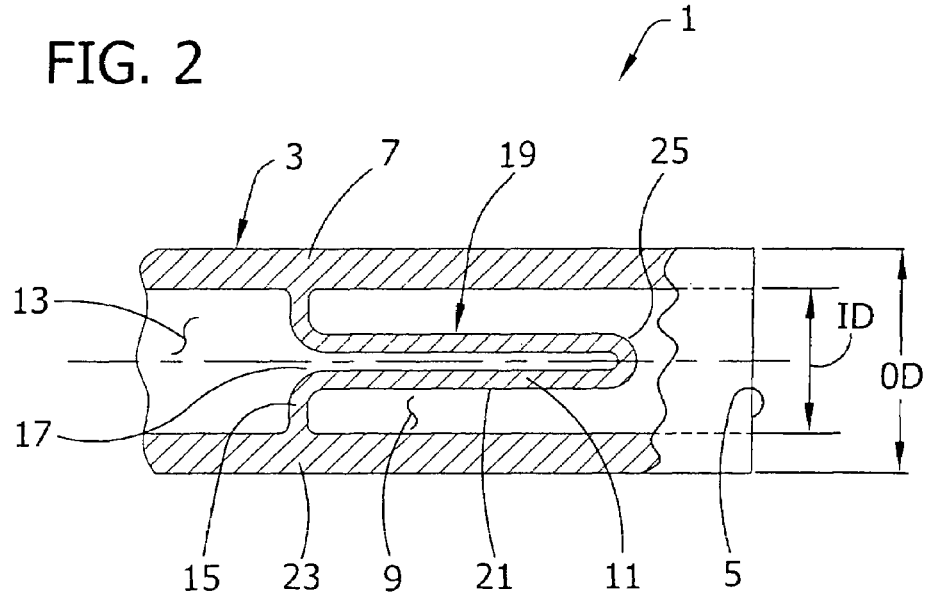
FIG. 2 is a enlarged view of a portion of FIG. 1, parts being broken away to show one of the recessed frangible seals.

Referring to FIG. 2, each seal 11 comprises a partition 15 extending across the interior 9 of the tube 3. The partition 15 is sealingly affixed along its periphery to the tubular wall 7 of the tube 3 thereby forming a sealing connection with the wall. The partition 15 has a fluid flow opening 17 in its center for allowing the flow of fluid into and out of the the sealed chamber 13 of the tube 3. Indicated generally at 19 is a frangible sealing element comprising a tubular post 21 which projects from the partition 15 in a direction away from the sealed chamber 13. In one embodiment the post 21 has a circular cross-section, but it may have other configurations without departing from the scope of this invention. Also, the post may be non-tubular (e.g., solid) along a portion of its length. The post 21 has a first open end 23 communicating with the fluid flow opening 17 and the sealed chamber 13, and a second closed end 25 opposite the open end. The closed end 25 preferably terminates in a free end located in the interior 9 of the tube 3, i.e., the free end of the post does not project out beyond the end 5 of the tube 3. The closed end 25 of the post 21 is adapted to be selectively broken to open the fluid flow opening 17 for use of the fluid sampling device 1 to sample fluid.

In one embodiment, the partition 15 of each seal 11 is sealingly affixed along its periphery to the interior 9 of the tube 3 by means of a ring seal. A ring seal is a glassblowing technique wherein the tube 3 is placed on a lathe for rotation of the tube on its axis. The post 21 is supported in the interior 9 of the tube 3 with the partition 15 in the desired position. A flame is used to evenly heat a narrow band on the tube 3 adjacent the partition 15 as the tube is rotated. The flame causes the glass tube 3 and glass partition 15 to become hot enough to flow together forming the seal. It is understood that the seal between the tube 3 and the partition 15 may be formed using other methods.

Figure 3:
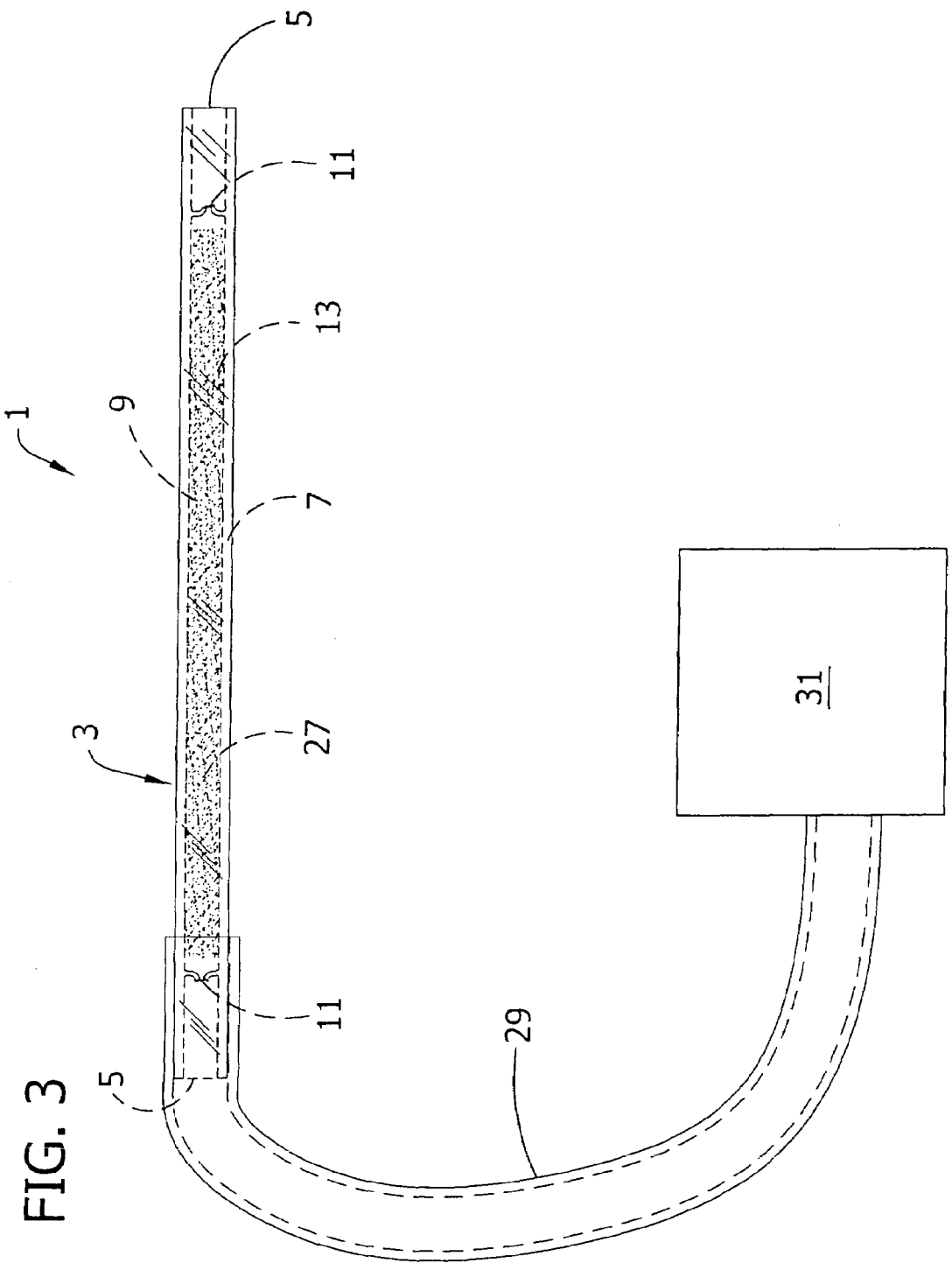
FIG. 3 is a view of the air sampling device with opened seals connected to a pump by means of flexible tubing.

Referring to FIG. 3, a fluid sampling media 27 is placed within the sealed chamber 13 for adsorbing or otherwise retaining a contaminate within the interior 9 of the tube 3. The sampling media 27 may be in the form of a filter, granular charcoal, granular carbon, silica gel or other sampling media known to those skilled in the art. Permeable retaining plugs (not shown), such as glass wool or urethane foam, may be used to hold the sampling media 27 in place within the sealed chambered. The media 27 used will vary depending on the types of fluid being sampled (e.g., air or liquid).

In the illustrated embodiment, the sampling device 1 has a length L of approximately 12 cm (FIG. 1), an inside diameter ID of approximately 4 mm and an outside diameter OD of approximately 6 mm (FIG. 2). The free ends of the posts 21 are recessed approximately 3 mm from respective open ends 5 of the tube 3 and the posts have a length of approximately 9 mm (FIG. 2). The sealed chamber 13 of the sampling device 1 between the partitions 15 has a volume of approximately 1.2 ml or 1,200 cubic mm. These dimensions are exemplary only and it will be understood that the sampling device 1 may have other dimensions and configurations without departing from the scope of this invention.

Figure 4:
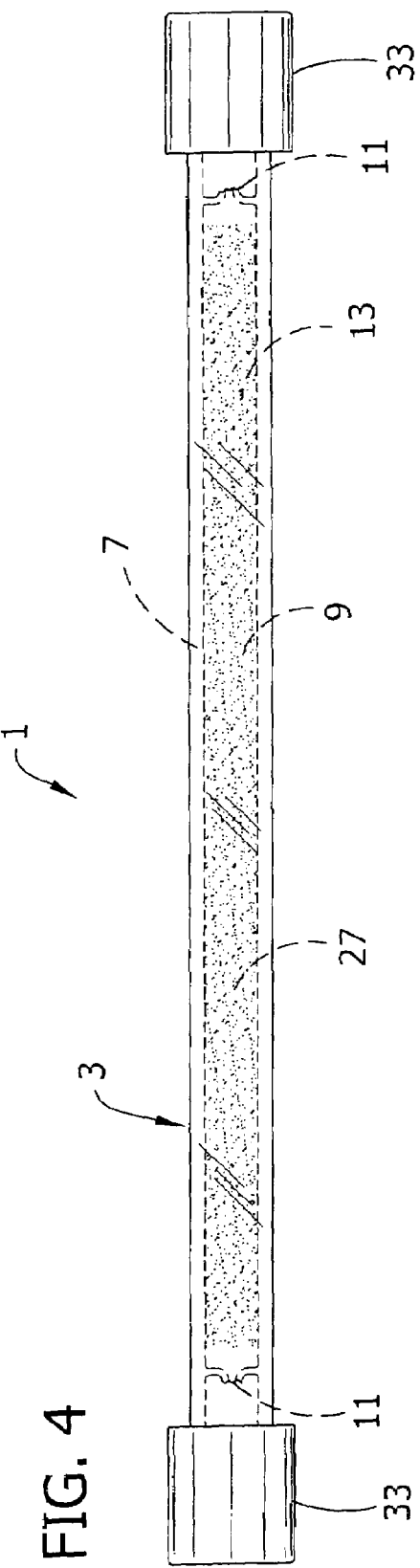
FIG. 4 is a view of the air sampling device with capped ends.

In operation, a sampling technician at the desired sampling location inserts a tool (not shown) or suitable implement, such as a pencil, into one of the open ends 5 of the fluid sampling device 1 to engage one of the frangible sealing elements 19. Using the tool, the technician safely breaks off the closed end 25 of the frangible post 21 thereby opening the fluid flow opening 17 which is in fluid communication with the sealed chamber 13. The severed closed end 25 is removed from the interior 9 of the tube 3 and discarded. The technician then follows the same steps to break and remove the opposite post 21. After both seals 11 are broken, the sampling device is attached at one end to tubing 29 (FIG. 3). Suitable tubing is commercially available from Sigma-Aldrich Co. of Saint Louis, Mo., USA as TYGON® Flexible Tubing. The opposite end of the tubing is connected to a pump 31, as shown in FIG. 3. Suitable pumps are commercially available from Sigma-Aldrich Co. of Saint Louis, Mo., USA such as the Model 1062 Air Sampler and the Model 1060 Air Sampler if the desired fluid to be sampled is air. The technician then places the sampling device 1 in a position so the unattached end is free from obstruction and within the area from which a fluid sample is to be collected. A predetermined volume of fluid is then drawn by the pump 31 through the fluid sampling device 1, following which the tubing 29 is disconnected from the sampling device 1. Plastic caps 33 are then applied to the end 5 of the tube 3 to substantially seal the tube, as illustrated in FIG. 4. The sample is then typically labeled and transported to a laboratory for analysis. It is understood that the sample may be collected in the sampling device 1 using other suitable sampling methods.

As will be observed from the foregoing, the sampling device 1 can be used to safely collect samples of contaminated fluids and improve the potential integrity of the sample. The sampling device 1 poses less risk of injury to the sampling technician since there are no exposed jagged edges. Further, the ends 5 of the sampling device 1 provide smooth even surfaces amenable for good sealing connection with both the polymeric tubing 29 (FIG. 3) and the plastic caps 33 (FIG. 4). Accordingly, the potential for leakage between the pump 31 and the device 1 and the potential for the caps 33 being damaged when applied to the tube ends 5 is minimized.

Figure 5:
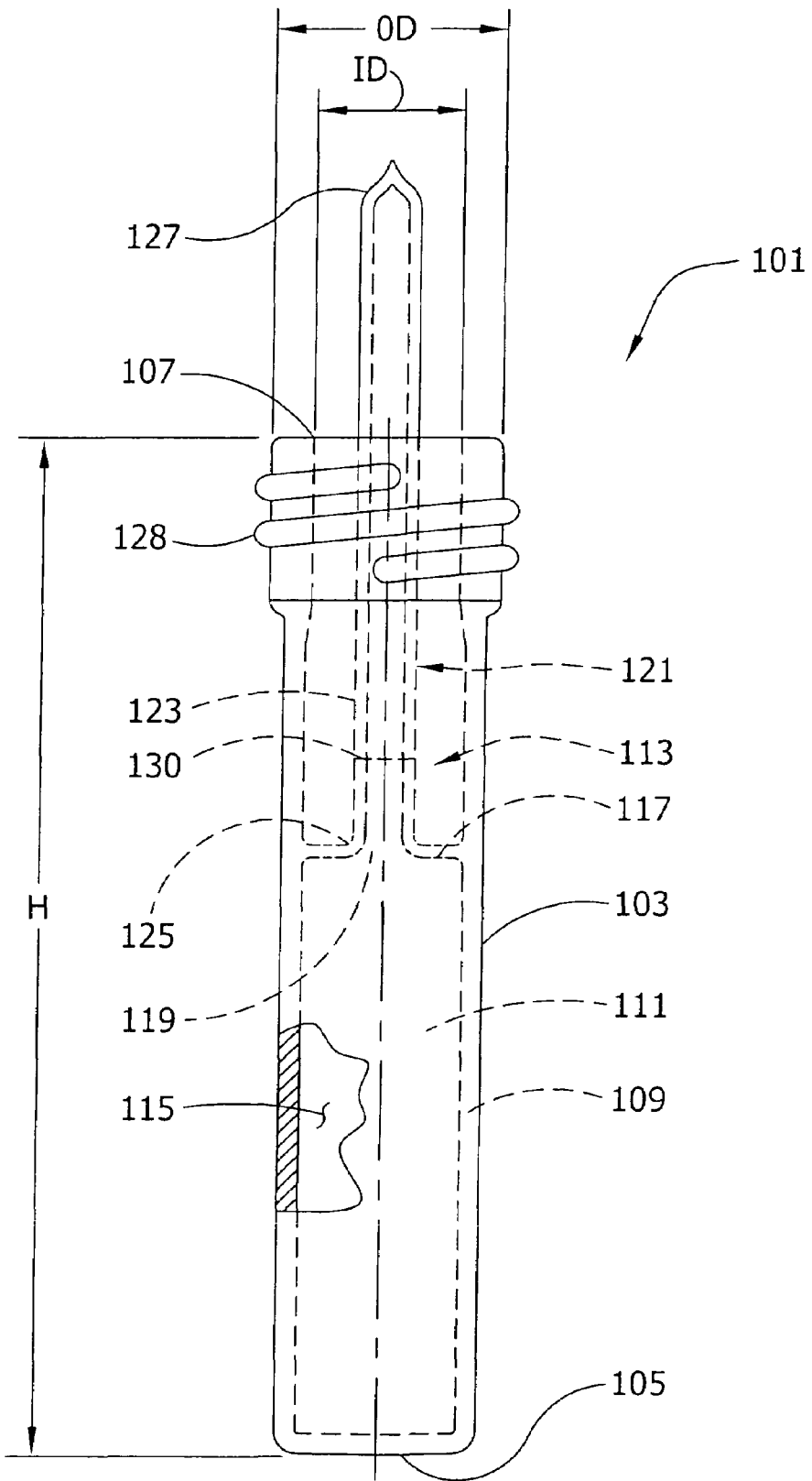
FIG. 5 is a view of one embodiment of a vial with a frangible seal.
Figure 6:
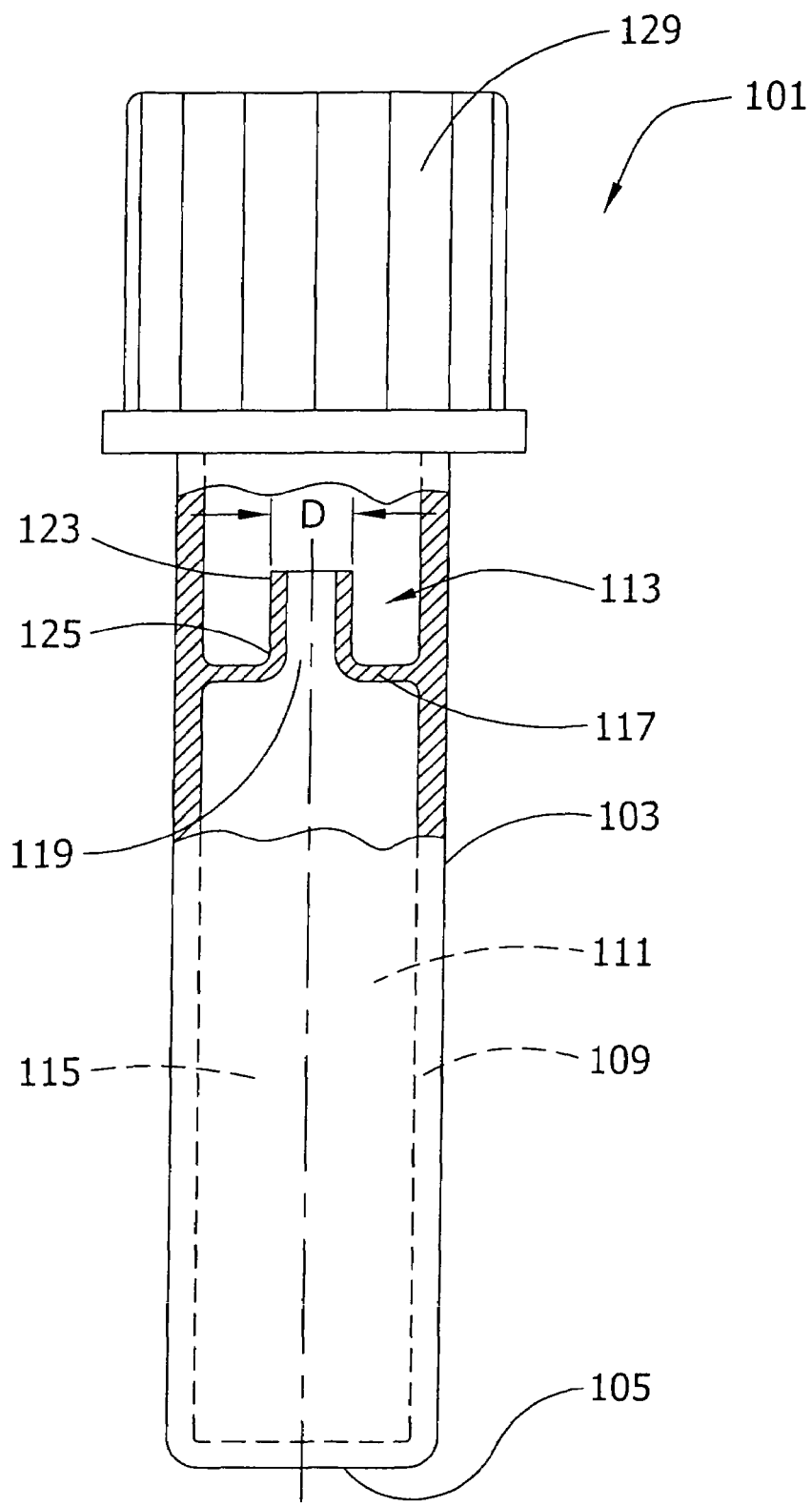
FIG. 6 is a view of the vial with the frangible seal broken and a removable cap secured to the vial.

FIGS. 5 and 6 show another embodiment of this invention comprising a container in the form of a vial, generally designated 101, for holding fluids. The vial includes a body 103 having a first end being closed by a bottom wall 105, a second open end 107 opposite the first end, and at least one wall 109 defining an interior 111 of the body. The wall 109 of the vial 101 may be cylindric, as illustrated, or have other non-circular shapes. The illustrated vial 101 is made of glass, however the vial may be made from other suitable materials.

A seal, indicated generally at 113, is sealingly connected to the wall 109 of the body 103 thereby defining a sealed chamber 115 within the body between the seal 113 and bottom wall 105 of the vial 101. The sealed chamber is used to seal fluids within the vial 101. The seal 113 is a frangible seal comprising a partition 117 spaced from the second end 107 of the vial 101. The partition 117 extends across the interior 111 of the body 103 and has a sealing connection to the wall 109 of the vial 101 around the periphery of the partition. The sealing connection between the partition 117 and the vial 101 may be formed using a ring seal technique, as described above, or other suitable methods. The partition 117 has a fluid flow opening 119 in its approximate center.

The seal 113 also includes a frangible sealing element, indicated generally at 121, connected to the partition 117 for sealing the opening 119. The frangible element 121 projects from the partition 117 in a direction away from the sealed chamber 115 and, in one embodiment (FIG. 5) comprises a tubular post 123. In one embodiment the post 123 has a circular cross-section, but it may have other configurations without departing from the scope of this invention. Also, the post may be non-tubular (e.g., solid) along a portion of its length. The post 123 has a first open end 125 communicating with the fluid flow opening 119 of the partition 117 and the sealed chamber 115, and a second end 127 opposite the open end. The second end 127 is initially open to allow filling of the sealed chamber 115 of the vial 101 with a fluid. The sealed chamber 115 may be filled using a pipet, a syringe needle or other suitable implement. Once the desired volume of fluid is dispensed into the sealed chamber 115, the second end 127 is closed (as shown in FIG. 5) thereby containing the fluid within the vial 101. The closure of end 127 may be effected by flame sealing or other suitable technique. The post 123 is adapted to be selectively broken to open the fluid flow opening 119 for dispensing fluid from the vial 101. The post 123 may be scored around all or part of its circumference to create a line 130 of weakness to control the location of the break. As shown in FIG. 6, the post 123 is preferably broken below the second end 107 of the vial 101 thereby allowing a screw-on cap 129 to be screwed on the threads 128 of the vial 101.

In the illustrated embodiment, the second end 127 of the post 123 extends beyond the second end 107 of the vial 101 to facilitate sealing (e.g., flame sealing) the second end closed. In this embodiment, the protruding portion of the post 123 is packaged to prevent the post 123 from breaking prematurely during shipping. Also included in the package is the cap 129 unattached to the vial 101. Alternatively, the second end 127 of the post 123 may be located within the interior 111 of the vial 101 without departing from the scope of this invention. In this embodiment, the cap 129 may be screwed onto the vial 101 before the vial is packaged for shipment.

In the illustrated embodiment, the chamber 115 of the vial 101 has a capacity of about 1.5 ml. The vial 101 has an approximate height H of about 50 mm, an outer diameter OD of about 10 mm and an inner diameter ID of about 8 mm (FIG. 5). The partition 117 is recessed from the second end 107 of the vial 101 approximately 20 mm. The post 123 has an outside diameter D of approximately 4 millimeters (FIG. 6). These dimensions are exemplary only, and it will be understood that the vial may have other dimensions and configurations without departing from the scope of this invention.

To remove fluid from the vial, a tool (not shown) or other suitable implement is used to break off the closed end 127 of the post 123 (preferably, along the line of weakness 130) thereby opening the fluid flow opening 119 which is in fluid communication with the interior 111 of the sealed chamber 115. The severed closed end 127 of the post 123 is removed and discarded. The consumer then removes a desired amount of fluid from the vial 101 using, for example, a micro-pipet or syringe needle. When finished, the consumer screws the cap 129 onto the threads 128 at the second end 107 of the vial 101 thereby resealing the remaining fluid in the vial for future use (FIG. 6).

It will be observed from the foregoing that the vial 101 can be used to transport and store fluid in an isolated environment while protecting it from evaporation, volatilization or other forms of degradation until the seal on the vial is broken by a consumer. After use, the vial 101 can be resealed to preserve any remaining fluid for subsequent use. The vial 101 can be used to store numerous fluids, and it may have different sizes and shapes without departing from the scope of this invention.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A container for receiving fluids comprising:
a body having opposite ends and at least one wall defining an interior space;
at least one seal defining a sealed chamber within the interior space of the body for receiving fluids, each seal having a sealing connection with said at least one wall of the body and being recessed from one of said opposite ends of the body;
fluid sampling media disposed within said sealed chamber; and
a cap for sealingly closing each end of said body having a seal recessed therefrom.

2. A container as set forth in claim 1 wherein said body is a tube, and wherein said at least one wall is a tubular wall.

3. A container as set forth in claim 2 wherein said at least one seal comprises two seals.

4. A container as set forth in claim 3 wherein said seals comprise frangible seals.

5. A container as set forth in claim 4 wherein each of said frangible seals comprises a partition extending across the interior of the tube and having a sealing connection to said tube around a periphery of the partition, an opening in said partition, and a frangible sealing element connected to said partition and sealing said opening, said frangible element projecting from the partition in a direction away from said sealed chamber, said frangible element being adapted to be selectively broken to open said opening.

6. A container as set forth in claim 1 wherein said fluid sampling media comprises air sampling media.

7. A container as set forth in claim 1 wherein said body is a cylindrical body and wherein said opposite ends comprise a first closed end and a second end opposite the first end.

8. A container as set forth in claim 7 wherein said at least one seal comprises one frangible seal recessed from said second end.

9. A container as set forth in claim 8 wherein said frangible seal comprising a partition extending across the interior of the body and having a sealing connection to said wall around a periphery of the partition, a fluid flow opening in said partition, and a frangible sealing element connected to said partition and sealing said opening, said frangible element projecting from the partition in a direction away from said sealed chamber, said frangible element being adapted to be selectively broken to open said fluid flow opening.

10. A container as set forth in claim 9 wherein said fluid is a liquid.

11. A container as set forth in claim 1 wherein said body is made of glass.

12. A container as set forth in claim 1 wherein said fluid sampling media is selected from a group consisting of a filter, granular charcoal, granular carbon, and silica gel.

13. A container as set forth in claim 1 further comprising at least one permeable retaining plug for holding the fluid sampling media within the sealed chambered.

14. A container as set forth in claim 1 in combination with a pump for drawing a predetermined volume of fluid into the container.

15. A container for receiving fluids comprising:
- a body having opposite ends and at least one wall defining an interior space;
- at least one frangible seal defining a sealed chamber within the interior space of the body for receiving fluids, each frangible seal having a sealing connection with said at least one wall of the body and being recessed from one of said opposite ends of the body, each of said frangible seals comprising a partition extending across the interior of the body and having a sealing connection to said body around a periphery of the partition, an opening in said partition, and a frangible sealing element connected to said partition and sealing said opening, said frangible element projecting from the partition in a direction away from said sealed chamber, said frangible element being adapted to be selectively broken to open said opening, each of said frangible seals being made of glass; and
- a cap for sealingly closing each end of said body having a seal recessed therefrom.

16. A container as set forth in claim 15 wherein said body is a tube, and wherein said at least one wall is a tubular wall.

17. A container as set forth in claim 15 wherein said at least one seal comprises two seals.

18. A container as set forth in claim 15 in combination with a tool sized and shaped for insertion into one of the ends of the body to engage and break the frangible seal.

* * * * *